United States Patent [19]

Love

[11] Patent Number: 4,530,762

[45] Date of Patent: Jul. 23, 1985

[54] ANAEROBIC REACTOR

[76] Inventor: Leonard S. Love, 578 Minette Cir., Mississauga, Ontario, Canada, L5A 3B9

[21] Appl. No.: 594,180

[22] Filed: Mar. 28, 1984

[51] Int. Cl.³ .............................................. C02F 3/28
[52] U.S. Cl. .................... 210/603; 210/188; 210/194; 210/521; 210/539
[58] Field of Search .............. 210/613, 188, 144, 521, 210/537, 539, 540, 603

[56] References Cited

U.S. PATENT DOCUMENTS

| | | | |
|---|---|---|---|
| 2,458,431 | 1/1949 | Schlenz | 210/613 X |
| 2,847,379 | 8/1958 | Spiegel et al. | 210/613 X |
| 3,279,606 | 10/1966 | Cox | 210/539 |
| 4,062,770 | 2/1977 | Kneer | 210/613 |
| 4,253,956 | 3/1981 | Pette | 210/188 |
| 4,346,005 | 8/1982 | Zimmermann | 210/521 X |
| 4,391,704 | 7/1983 | Anderson | 210/539 X |
| 4,401,565 | 8/1983 | Schimel | 210/539 X |

Primary Examiner—Thomas Wyse
Attorney, Agent, or Firm—Rogers, Bereskin & Parr

[57] ABSTRACT

A method and apparatus for the anaerobic treatment of wastewater containing organic matter. The apparatus includes a closed tank to which the wastewater is delivered through liquid inlet means below a reaction hood. The reaction hood defines a mixing zone in which influent water mixes with liquid and biological solids already in the zone. A portion of the liquid being mixed is withdrawn and passed through a gas separator which removes entrained gas and returns the liquid to the tank. The tank may include fixed film media for improving treatment efficiency. Other features of the invention are the use of a sludge thickener for concentrating sludge removed from the tank and the use of a second gas separator in a treated effluent conduit from the tank. That separator has an adjustable baffle or weir which can be raised to flush scum into surface launders in the tank.

16 Claims, 1 Drawing Figure

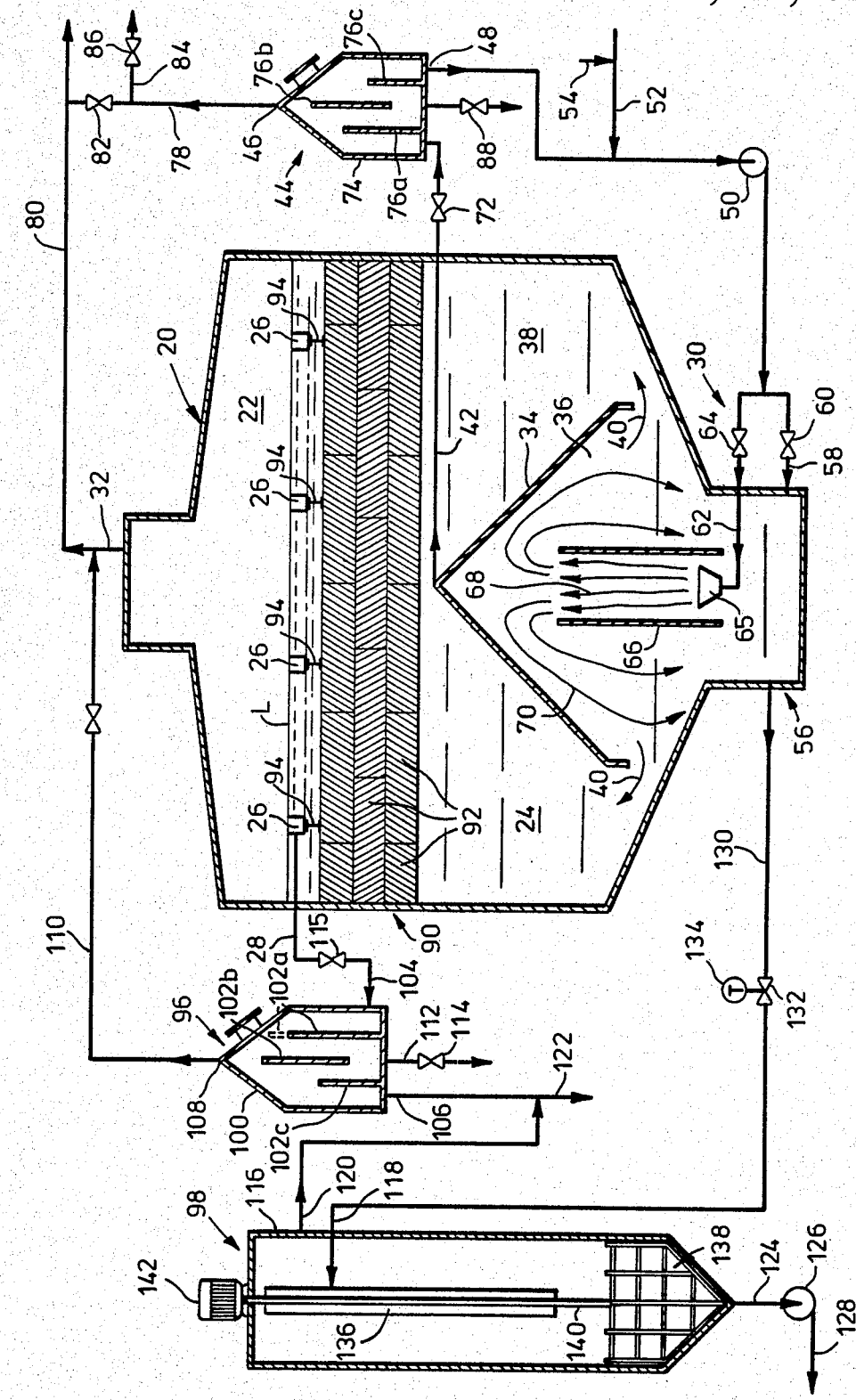

ANAEROBIC REACTOR

This invention relates generally to a method and apparatus for the anaerobic treatment of wastewater containing organic matter.

Anaerobic treatment of wastewater is a biological process in which saprophytic bacteria feed on the organic matter in the absence of oxygen, and at elevated temperature. The products of the process are carbon dioxide and methane gas. Organic solids in the wastewater are first liquified by the action of enzymes and then broken down by the action of two different groups of bacteria, commonly called "acid formers" and "methane formers".

The anaerobic treatment process takes place in three separate steps which must be in harmony for the process to work efficiently. The steps are:

(A) ACID FERMENTATION

During this step acid forming bacteria first convert organic matter (carbohydrates, proteins, fats) into simple volatile acids (acetic acid, propionic acid, butyric acid).

(B) ACID REGRESSION

During this stage, decomposition of volatile fatty acids (fats, oils and waxes) and soluble nitrogen compounds (proteins) takes place. This results in the formation of ammonia, amines and acid carbonates.

(C) ALKALINE FERMENTATION

This step limits the rate at which the overall process proceeds. Volatile acids and volatile fatty acids produced by the acid formers are broken down by the methane formers to produce carbon dioxide and methane gas.

In order for these three steps to work in harmony, the pH of the liquid being treated must remain within controlled limits. The methane formers are particularly sensitive to pH level and the pH must not be allowed to drop below about 6.7 to 7.0 if the process is to operate satisfactorily. The difficulty of maintaining the pH of the liquid within the defined limits is compounded by the fact that the acid forming bacteria reproduce vigorously and are less sensitive to environmental factors than the slower reproducing methane formers. This can result in an excess of volatile acids derived from the acid fermentation step. Conversely, during acid regression, the pH will tend to increase due to the formation of ammonia.

So-called "anaerobic digesters" have been used widely in municipal sewage treatment for the stabilization (odour removal) of waste biological sludge prior to final disposal. In view of economic considerations, proposals have also been made to use anaerobic reactors for the treatment of high strength wastewater. Generally, as compared with aerobic treatment processes, anaerobic treatment is perceived to require less energy, and produce less waster biological sludge. Also, there is an increasing recognition of the value of the methane gas produced by anaerobic processes. Prior to the oil crisis of 1973, the methane gas produced by anaerobic digesters in municipal sewage treatment was generally not recovered but was burned off through a flare. However, today, almost all plants find it economical to recover and use the methane gas.

Anaerobic reactors for wastewater treatment were initially designed on the basis of experience with the anaerobic digestion of municipal sewage sludges. However, it was soon recognized that the two applications of anaerobic treatment are quite different. In the treatment of municipal sewage, sludges have first undergone aerobic biological treatment process and are therefore highly buffered and normally are sufficiently alkaline to maintain the reactor at a pH of 6.8 or greater. The absence of buffering in the anaerobic treatment of high strength wastewater creates a demand for alkalinity (usually caustic soda) to be added continuously to wastewater to maintain the pH within the required range of approximately 6.7 to 7.0 by neutralizing the high level of volatile acids produced:

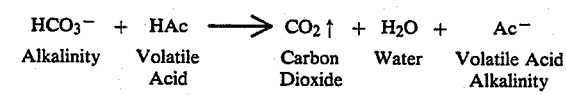

| $HCO_3^-$ | + | HAc | $\longrightarrow$ | $CO_2 \uparrow$ | + | $H_2O$ | + | $Ac^-$ |
|---|---|---|---|---|---|---|---|---|
| Alkalinity | | Volatile Acid | | Carbon Dioxide | | Water | | Volatile Acid Alkalinity |

Thus, production of carbon dixoide (and methane gas) is much greater than with municipal sewage.

The excess carbon dioxide produced by this reaction creates a partial pressure which causes the carbon dioxide to dissolve and form carbonic acid; this in turn causes the pH to drop requiring the addition of further caustic soda.

The volume of carbon dioxide produced in practice is so high that large quantities of caustic soda must be added to the system to neutralize the additional acid demand which occurs in the treatment of high strength wastewater. It has in fact been reported that, at some installations, the cost of caustic soda required to maintain the pH at the required level is greater than the value of the methane gas produced.

Another problem created by the excessive gas production in an anaerobic system is that it has a buoyant effect on the biological solids generated during the anaerobic reaction. Gas bubbles rising in the wastewater tend to cause these solids to rise and leave the system as part of the treated effluent. Since these solids contain the bacteria which are essential to the reaction, the loss of these solids is detrimental to the operation of the reactor.

A primary objective of the present invention is to address these problems in the anaerobic treatment of high strength wastewaters. Specific objectives are to reduce the demand of the system for alkalinity, reduce the loss of biological solids from the system and improve system and improve treatment efficiency.

According to one aspect of the present invention there is provided an anaerobic reactor which includes a tank defining a closed chamber for receiving a body of liquid, liquid inlet means disposed in a lower region of the tank and through which wastewater to be treated can be introduced into the tank, treated water outlet means in an upper region of the tank and a gas outlet above the liquid level in the tank. A reaction hood is disposed in the tank above the liquid inlet means and defines a mixing zone below the hood and a relatively quiescent zone outside the hood into which liquid can escape around marginal portions of the hood. The inlet means is adapted to cause wastewater entering the tank from the inlet means to promote mixing of liquid in said mixing zone. An outlet is provided within the hood through which mixed liquid and entrained gas can be withdrawn. The reactor also includes a gas separator having an inlet coupled to the hood outlet and respective outlets for the separated gas and liquid. Means is provided for recycling separated liquid from the gas separator to the tank liquid inlet means.

When the reactor is in operation, wastewater to be treated will continually flow into the tank through the liquid inlet means and treated water will leave the tank through the treated water outlet means. As discussed previously, the products of the anaerobic treatment process are carbon dioxide and methane gas. The methane gas will be withdrawn through the gas outlet above the liquid level in the tank and collected or used at a remote location. Suitable valving will normally be provided for controlling release of gas from this outlet. The mixture under the reaction hood will comprise liquid biological sludge containing bacteria and entrained carbon dioxide and methane gas. A portion of this mixture will be withdrawn from the hood and delivered to the gas separator, from where the liquid will be recycled back to the tank. If the gas removed in the separator is mostly carbon dioxide, it may be simply vented to atmosphere but if it contains significant quantities of methane it will be collected, for example by being directed to the same line as the main gas outlet from the tank.

Liquid will also flow from around the margin of the hood up through the quiescent zone of the tank towards the treated water outlet means. Settling will take place in the quiescent zone and the settled solids will gradually return to the main body of biological sludge.

It is believed that, by removing part of the reaction gases at the lower level of the tank (within the hood), the need for the addition of alkalinity to the system can be reduced. Where additional alkalinity is required, it can be fed into the main wastewater inlet. In fact, it is believed that a large part of the gas withdrawn at the reaction hood will be carbon dioxide, which will reduce the amount of carbonic acid formed. At the same time, it is believed that loss of biological solids from the system will be reduced and treatment efficiency improved.

The invention also provides a method of anaerobic treatment of wastewater, comprising providing a tank defining a closed chamber; continuously introducing wastewater to be treated into a body of liquid in said chamber; mixing said liquid in a lower region of the chamber; withdrawing a portion of said liquid and entrained gas from said region; separating the gas from said portion while retaining the remainder of the liquid to the chamber; continuously removing treated water from an upper region of the chamber; and removing gas from the chamber at a level above the level of liquid therein.

In order that the invention may be more clearly understood, reference will now be made to the accompanying drawing which illustrate a preferred embodiment of the invention by way of example.

The drawing is a schematic diagram of an aerobic reactor in accordance with the invention.

Referring to the drawing, reference numeral 20 indicates a treatment tank defining a closed chamber 22 for receiving a body 24 of liquid. The liquid extends to a level indicated at L in the drawing. A series of launders 26 extend across the tank and are connected to a common collecting pipe 28. Treated water leaves the tank by overflowing into the launders as is conventional in the water treatment art.

Liquid inlet means generally indicated at 30 is provided for introducing liquid to be treated into a lower region of the tank. A gas outlet denoted 32 is provided at the top of the tank for removing methane gas which tends to collect in the space above the liquid when the system is in operation.

A reaction hood 34 is disposed in the tank above the liquid inlet means and defines a mixing zone 36 below the hood and a relatively quiescent zone 38 outside the hood into which liquid can escape around marginal portions of the hood as indicated by the arrows denoted 40. The inlet means 30 (to be described in detail below) are arranged to cause wastewater entering the tank to promote mixing of liquid in the mixing zone 36 and in fact it is anticipated that substantially complete mixing will be achieved within that zone.

An outlet pipe 42 is coupled to the top of the reaction hood and extends through the wall of the tank to a gas separator 44. Separator 44 has an outlet 46 for separated gas and an outlet 48 for liquid. Outlet 48 is coupled by way of a recycle pump 50 to the liquid inlet means 30. A main wastewater inlet line is coupled to the line from outlet 48 to pump 50 and is denoted by reference 52. Alkalinity (if required) can be introduced into the incoming wastewater through an alkalinity feed-line 54. In other words, the caustic soda (or other alkaline material) is added directly into the wastewater at the suction side of the recycle pump which promotes complete mixing of the alkaline material with wastewater.

Tank 20 may typically be a metal or concrete tank and includes a sludge sump at the center of its bottom wall. Wastewater can be introduced into the tank either at the base of the sludge sump through an inlet line 58 controlled by a valve 60 or at the top of the sludge sump though an inlet line 62 controlled by a valve 64. Inlet 58 is arranged so that the incoming liquid imparts a swirling motion to the entire contents of the sump for promoting mixing. Inlet 62 is coupled to an nozzle 65 disposed within a vertical tubular conduit 66 arranged to constrain the incoming liquid to flow generally vertically upwardly as indicated by the arrow 68. The liquid will then flow outwardly and down within the reaction hood 34 and re-enter the lower end of the conduit 66 for recirculation. A pressure nozzle will impart sufficient velocity to the incoming wastewater to promote complete mixing and solids recirculation under the reaction hood.

It will of course be apparent to a person skilled in the art that a reactor of the form being described will be self sustaining when started. At start up, the liquid may be "seeded" with bacteria and alkaline material in appropriate quantities to promote the required biological reaction within the chamber and achieve an appropriate pH level. However, once a satisfactory reaction has been established, the reaction will be self-sustaining provided a proper pH level is maintained and flow rates through the reactor are properly controlled. Thus, the incoming wastewater will be continuously mixed within the reaction zone, with biological sludge containing acid forming and methane forming bacteria already in the tank.

Introduction of incoming wastewater through nozzle 65 has the advantage of allowing sludge compaction below the nozzle when the sludge is to be removed on a batch basis.

Whichever mode of introducing the wastewater is selected, it is anticipated that the biological sludge concentration under the reaction hood will be in the order of 40,000 to 60,000 mg./L and complete mixing will be obtained. The mixture under the reaction hood will include liquid bioligical sludge containing bacteria as well as carbon dioxide and methane gas. It is expected that 50% (or more) or the entire carbon dioxide production will occur under the reaction hood.

A portion of this mixture will be withdrawn from the top of the reaction hood through line 42 under the control of a recycled control valve 72. It is anticipated that the recycle rate may be from 50-500% of the rated capacity (through-flow volume) of the reactor. Valve 72 will be set to provide the recycle rate considered appropriate for the particular wastewater being treated.

Gas separator 44 is essentially of conventional construction in itself and comprises a housing 74 containing baffles 76a, 76b and 76c. In flowing to the liquid outlet 48 the liquid delivered through line 42 flows sequentially over baffle 76a, under baffle 76b and over baffle 76c. Baffles 76a and 76c thus act as weirs. This causes entrained gas to be liberated and the gas leaves housing 72 through outlet 46. Outlet 46 is connected to a line 78 which in turn joins a main gas collection line 80 from the gas outlet 32 of tank 20. A valve 82 is provided in line 78 and a vent line 84 controlled by a valve 86 extends from line 78 upstream of valve 82. It is anticipated that the gas separated in separator 44 will be primarily carbon dioxide. If this is the case, valve 82 will be closed and valve 86 opened and the gas vented to atmosphere. Alternatively, if the gas is deteremined to contain methane, valve 86 will be closed and valve 82 opened and the methane fed into the main methane line 80. As has been discussed previously, if the gas is primarily carbon dioxide, then removing that gas from within the mixing zone 36 will have the effect of reducing production of carbonic acid within the liquid being treated. This, in turn, will allow the pH level to be kept up within the tank while minimizing the need for addition of alkalinity.

A blow down outlet 88 is provided in the housing of gas separator 44 for cleaning purposes.

Continuous introduction of liquid into tank 20 through the liquid inlet means 30 will cause liquid to continuously leave the mixing zone below the hood 34 around the lower periphery of the hood as indicated by the arrows 40. This liquid will flow upwardly in the tank towards the launders 26 through the quiescent zone 24, where settling will take place. Settled solids will gradually find their way to the sludge sump 56 at the bottom of tank 20.

In the embodiment shown in the drawing, the reactor includes a bed 90 of so-called "fixed film media" disposed above the quiescent zone 24. This media is formed by a series of "tube settler bundles", each of which defines an array of inclined tubes through which water can flow. Typically, a tube settler bundle is made in the form of a rectangular block formed by heat welding together sheets of corrugated plastic arranged so that the corrugations form water passageways through the block. Tube settlers are well-known for use in clarifiers and are available from the Munters Corporation of Fort Myers, Fla. My U.S. patent application Ser. No. 510,140 filed July 1, 1983 discloses improvements relating to tube settlers. In any event, as shown in the drawing of the present application, the bed 90 of fixed film media is formed by three layers of tube settler bundles 92 which cover the surface of the liquid in tank 20. Typically, each bundle will be of a size of 4 or 8 feet long by 2 feet wide by 1 or 2 feet deep, which means that the total depth of the media bed 90 will be approximately 3 or 6 feet in the illustrated embodiment. However, the depth of the bed may in fact vary quite widely, preferably within a range of 2 to 6 feet (or greater).

The principle of operation of tube settlers is well-known in the water treatment art. As water rises generally vertically into the lower ends of the tubes, particles carried by the water come into contact with portions of the inner walls of the tubes in their path, by virtue of the fact that the tubes are inclined. This has the effect of causing those particles to settle out of the water and fall down onto lower surface portions of the inside walls of the tubes, where the particles tend to concentrate. Eventually, the mass of particles reaches a state at which the mass will slide down the lower surface of the tube settler into the liquid below. At this point, the particles have been removed from the liquid being treated, and become components of a sludge mass.

By utilizing tube settlers in the environment of an anaerobic reactor, it is believed that the efficiency of biological solids removal will be improved as compared with an anaerobic reactor without tube settlers. This should serve to improve the quality of the effluent from the reactor because the effluent will contain less suspended solids than a reactor without tube settlers.

Further, it is believed that the anaerobic organisms within the treatment liquid will attach to the media and grow and thereby be be retained within the system. This should greatly increase treatment efficiency and methane production.

Preferably, the tube settler bundles will be of a design providing a so-called "cross flow" pattern. In other words, the bundle will be designed to provide passageways angled in opposite directions within the same bundle for even distribution of water across the bundle. This feature is significant because it will ensure complete utilization of the entire reactor volume. Cross flow tube settler bundles are available from the Munters Corporation.

Bed 90 will be supported in the reactor tank 20 by suitable supporting structure (not shown). For example, this structure may take the form of a latticework or grid of channels extending across the reactor and on which the tube settler bundles rest.

In the illustrated embodiment, the bed 90 also itself serves as a support for the launders 26 through which treated water is removed from the reactor. The launders are essentially upwardly facing channels which are disposed in horizontal positions within the tank 20 and are levelled with respect to one another so as to define the level L of liquid within the tank. As liquid continuously enters the tank from the liquid inlet means 30, treated liquid is continuously flowing over the side limbs of the channels forming the the launders 26 and into the channels themselves. The launders are interconnected and flow into conduit 28 through which treated liquid leaves the reactor. As shown in the drawing, each launder 26 is supported by an I-shaped member 94 (metal or plastic) to which the launder is attached and which itself simply rests on the top surface of bed 90.

As discussed previously, while it is believed that the use of a media bed 90 offers significant advantages, the media bed is not essential within the the broad scope of the invention. In some applications, the media bed can be eliminated completely. It is anticipated that this will reduce in somewhat reduced treatment efficiency as compared with a reactor containing the media bed; however, the capital cost will not be as great and the treatment efficiency may be acceptable in some applications. For example, such treatment could be adequate where it is intended to provide primary treatment only, possibly followed by aerobic or chemical treatment.

The fact that the anaerobic process converts all organic matter into short chain volatile acids makes this process particularly suitable for a primary treatment step preliminary to an aerobic biological process.

Anaerobic treatment without the media bed 90 is also well suited to the treatment of certain wastewaters from the pulp and paper industry and from other industries having wastewater with a high calcium content. It has been found that the calcium tends to deposit as a calcium carbonate scale on the fixed film media to the point where the media can become completely plugged over a period of time (e.g. two to three years). It is believed that this is due to conversion of calcium bicarbonate from the wastewater into calcium carbonate scale (with attendant production of water and carbon dioxide) at the operating temperature typically found within an anaerobic reactor (e.g. of the order of 95° F.). Obviously, in applications such as this it is not appropriate to use a fixed film media bed.

Where there is no fixed film media bed, the reaction hood may be made somewhat larger and could even by dimensioned so that its apex is disposed just below the water level L in tank 20.

In the illustrated embodiment, the reactor tank 20 is shown associated with a second gas separator generally denoted 96 and with a sludge thickener 98. Thickener 98 is a preferred (though optional) feature of the invention. Where submerged launders are used, gas separator 96 is not required.

The gas separator 96 is in principle similar to separator 44 it that it comprises a housing 100 having three internal baffles 102(*a*), 102(*b*) and 102(*c*), of which baffles 102(*a*) and (*c*) act as weirs. The housing has a liquid inlet 104, a liquid outlet 106 and a gas outlet 108. Treated liquid entering housing 100 from tank 20 flows first over the primary weir formed by baffle 102(*a*) and, sequentially, under baffle 102(*b*) and over baffle 102(*c*) to outlet 106. During this flow methane gas which may be entrained within the treated water is released and leaves the housing 100 through gas outlet 108. That outlet is connected to the main methane gas outlet 32 from tank 20 by a line 110. Housing 100 also has a main "blow down" outlet 112 controlled by a valve 114 to permit the housing to be cleaned out periodically.

It will be appreciated that, in normal operation of the reactor, the weir 102(*a*) should be positioned with its top edge in horizontal alignment with the edges of the launders 26. In accordance with a preferred feature of the invention, this weir 102*a* is designed so that it can be periodically raised from this normal operating position to effectively raise the level of the liquid in tank 20. This will have the effect of causing the liquid to flush into the launders scum which will tend to collect on the surface of the liquid adjacent the launders adjacent the launders in normal operation of the reactor. This scum normally simply lies on the surface of the liquid and the liquid entering the launders flows out from under the scum so that the scum simply tends to accumulate. This represents a significant and serious sents a significant and serious problem in the operation of conventional anaerobic reactors. However, by the expedient of raising the adjustable weir 102(*a*) in the gas separator, the liquid level in tank 20 is temporarily raised and will have the effect of flushing the scum into the launders. The scum can then be collected in the gas separator 96 and periodically "blown down" from housing 100 when required. In the drawing, raising of baffle 102*a* is represented by an extension of that baffle shown in ghost outline. The mechanism by which the baffle would be raised and lowered has not been shown. Typically, the baffle would be located in guides which would allow vertical sliding of the baffle and a mechanical arrangement would be provided to permit the baffle to be raised and lowered from externally of the housing 100. In its simplest form, this could take the form or a cable or chain extending from baffle 102*a* through housing 100 to a location at which the cable or chain would accessible to an operator who would manually lift the baffle. Preferably, whatever arrangement is used should be designed not only to permit the baffle to be raised and lowered between two extreme positions, but should allow for the possibility of adjustment between those extreme positions so that the baffle can be used to control the operating level of the liquid in the reactor tank.

The use of this form of gas separator 96 has the advantage of allowing surface launders to be used to collect the treated effluent from the reactor, rather than submerged launders. With submerged launders, it is impossible to collect surface scum with the treated effluent; rather, the reactor must be shut down periodically for cleaning. Further, the use of surface launders allows the overall height of the reactor tank to be reduced as compared with the height required for a tank having submerged launders; in the latter case, the tank must be of sufficient height to allow a depth of water capable of accommodating the launders above the depth required for the normal reaction zone of the the reactor. It is anticipated that a reduction in height of at least one foot would be possible for reactors of equivalent capacity.

A shut-off valve 115 is of course provided in the line 28 through which treated effluent flows to the gas separator from the reactor tank.

Sludge thickener 98 is a further optional feature of the invention and is designed to permit continuous removal of waste biological sludge. Conventional practice in the art is to remove waste sludge from the reactor tank on a batch basis. This has two problems. First, the waste sludge is quite dilute and therefore the volume and cost of sludge disposal is high. Secondly, removal of large quantities of biological sludge at one time imposes a serious loss of working micro-organisms on the reactor and treatment efficiency suffers for a long period after sludge has been removed. It is believed that continuous sludge removal and thickening in accordance with the present invention will reduce the sludge volume and disposal costs significantly (e.g. 75–85%). Also, reactor treatment efficiency will not be impaired.

As shown in the drawing, thickener 98 includes a tank 116 having a sludge inlet 118 and a treated effluent outlet 120. Outlet 120 connects with the liquid outlet from gas separator 96 to form a common treated effluent discharge 122 from the system. Tank 116 also has a thickened sludge outlet 124 connected to a main disposal pump 126 to a sludge disposal outlet 128.

Sludge inlet 118 is connected to the sludge sump 56 of tank 20 by a line 130 which includes a valve 132 controlled by a timer 134. Timer 134 will be set to open on a predetermined repeating cycle to allow sludge to be discharged from sump 56 under the pressure of the head of liquid within tank 120.

Thickener tank inlet 118 is connected to a feed well 136 within tank 116. Influent sludge will flow down in feed well 136 and discharge into a lower region of tank 116. Feed well 136 takes the form of a cylinder arranged with its axis vertical and disposed centrally of tank 116.

The tank is provided with a mixer having a mixer blade 138 disposed in the lower region of tank 116 and coupled to the lower end of a vertical drive shaft 140 which extends up through the feed well 136 to a drive motor 142 supported at the top of tank 116. Motor 142 is designed to slowly rotate blade 138 within tank 116 to thicken the sludge within the tank in conventional fashion. Thickened sludge will be periodically blown down from tank 116 by pump 126 for disposal through outlet 128.

In summary, it is believed that the reactor provided by the invention will offer significant advantages compared with the prior art in terms of treatment efficiency and reduced alkalinity demand. At the same time, methane gas produced by the reaction is recovered for use as an energy source. Treatment efficiency can further be enhanced by the use of a fixed film media bed and additional advantages can be obtained by the use of a gas separator in the treated effluent discharge line and a sludge thickener. As discussed previously, these features are not essential within the broad scope of the invention.

It will of course also be understood by persons skilled in the art that many other modifications are possible within the broad scope of the invention. Also, it should be noted that the drawing to which reference is made herein is schemmatic only and does not show all constructional details. For example, both the main reactor tank 20 and the hood 34 are shown in vertical section only. As seen in plan, these elements will normally be of circular shape although this is not essential within the broad scope of the invention. For example, either or both of these elements could be of square or other rectangular shape in plan.

I claim:

1. An anaerobic reactor comprising:
   a tank defining a closed chamber for receiving a body of liquid;
   liquid inlet means disposed in a lower region of the tank and through which wastewater to be treated can be introduced into the tank;
   treated water outlet means in an upper region of the tank;
   a gas outlet above the liquid level in the tank;
   a reaction hood disposed in said tank above the liquid inlet means and defining a mixing zone below the hood and a relatively quiescent zone outside the hood into which liquid can escape around marginal portions of the hood, the inlet means being adapted to cause wastewater entering the tank from the inlet means to promote mixing of liquid in said mixing zone;
   an outlet within the hood through which mixed liquid and entrained gas can be withdrawn;
   a gas separator having an inlet coupled to said hood outlet and respective outlets for separated gas and liquid; and,
   means adapted to recycle separated liquid from the gas separator to said tank liquid inlet means.

2. A reactor as claimed in claim 1, wherein said gas outlet of the gas separator is coupled to said gas outlet above the liquid level in the tank, and to a vent, and wherein valve means are provided for permitting gas leaving said outlet to be directed to said vent or collected with gas leaving said tank outlet.

3. A reactor as claimed in claim 1, wherein said means adapted to recycle separated liquid from the gas separator to said tank liquid inlet means includes a recycle line incorporating a recycle pump, and wherein a main wastewater inlet line is provided upstream of said pump for delivering wastewater to be treated to said tank, and wherein said main inlet line includes alkalinity feed means by which alkaline material may be introduced into said wastewater for mixing by said recycle pump.

4. A reactor as claimed in claim 1, wherein said tank includes a sludge sump in a lower wall of the tank, and wherein said liquid inlet means comprises first and second inlets vertically spaced in said tank, and valve means adapted to control delivery of liquid through the respective inlets, said first inlet being disposed in said sump and being adapted to impart a swirling motion to material in said sump, and said second inlet being spaced above the first inlet and being adapted to direct influent liquid generally vertically upwardly below said reaction hood.

5. A reactor as claimed in claim 4, wherein said second inlet includes a inlet nozzle and a generally cylindrical conduit disposed in a substantially vertical position below said hood with said nozzle being arranged to direct liquid upwardly in said conduit.

6. A reactor as claimed in claim 1, further comprising a second gas separator having an inlet coupled to said treated water outlet means in the tank and respective outlets for gas separated from said liquid and treated effluent, said gas outlet being coupled to said gas outlet above the liquid level in the tank.

7. A reactor as claimed in claim 6, wherein said treated water outlet means includes a series of launders disposed at the surface of said body of liquid in the tank, and wherein said second gas separator includes an internal baffle defining a primary weir over which influent liquid flows, said weir defining the level of said body of liquid in the tank and being adjustable in height so that said level can be selectively raised to flush scum collected on the surface of said body into the launders for collection in said gas separator; and wherein said separator includes blow down means for removing accumulated scum.

8. A reactor as claimed in claim 1, further comprising a bed of fixed film media disposed in said tank below said treated water outlet means, said media defining an array of inclined water passageways providing paths for liquid flowing upwardly in said tank towards said treated water outlet means.

9. A reactor as claimed in claim 8, wherein said bed of fixed film media is defined by a series of layers of plastic tube settler bundles supported in said tank.

10. A reactor as claimed in claim 9, wherein said treated water outlet means comprises a series of launders disposed at the surface of said body of liquid and supported on said fixed film media bed.

11. A reactor as claimed in claim 1, wherein said tank includes a sludge sump in a lower wall of the tank and wherein the reactor further comprises a sludge thickener separate from said tank and including a thickener tank having a thickened sludge outlet in a lower region thereof, a sludge inlet coupled to said sludge sump and to said thickener tank at a level below the level of said body of liquid; means controlling flow of sludge from said sump to said thickener tank, a treated effluent outlet from said thickener tank and mixer means within said thickener tank for thickening sludge delivered to said tank.

12. A reactor as claimed in claim 11, wherein said means controlling delivery of sludge from said sump to said thickener tank comprises a timer controlled valve.

13. An anaerobic reactor including a tank defining a closed chamber for receiving a body of liquid, a gas outlet above the liquid level in the tank, liquid inlet means disposed in a lower region of the tank and through which wastewater to be trated can be introduced into the tank, and treated water outlet means in an upper region of the tank including a series of launders disposed at the surface of said body of liquid in the tank, wherein the improvement comprises a gas separator having an inlet coupled to said treated water outlet means and respective outlets for gas separated from said liquid and treated effluent, said gas separator including an internal baffle defining a primary weir over which liquid flows, the gas separator being arranged so that said primary weir defines the level of said body of liquid in the tank and said weir being adjustable in height so that said level can be selectively raised to flush scum collected on the surface of said body into the launders for collection in said gas separator, and wherein said separator includes blow down means for removing accumulated scum.

14. An anaerobic reactor including a tank defining a closed chamber for receiving a body of liquid, a gas outlet above the liquid level in the tank, liquid inlet means disposed in a lower region of the tank and through which wastewater to be treated can be introduced into the tank, and treated water outlet means in an upper region of the tank;

wherein the improvement comprises said tank including a sludge sump in a lower wall of the tank and wherein the reactor further comprises a sludge thickener separate from said tank and including a thickener tank having a thickened sludge outlet in a lower region thereof, a sludge inlet coupled to said sludge sump and to said thickener tank at a level below the level the level of said body of liquid, means controlling flow of sludge from said sump to said thickener tank, a treated effluent outlet from said thickener tank, and mixer means within said thickener tank for thickening sludge delivered to said tank.

15. A method of anaerobic treatment of wastewater comprising:

providing a tank defining a closed chamber;

continuously introducing wastewater to be treated into said chamber;

mixing said liquid in a lower region of the chamber;

withdrawing a portion of said liquid and entrained gas from said region;

separating the gas from said portion while returning the remainder of the liquid to the chamber;

continuously removing treated water from an upper region of the chamber; and, removing gas from the chamber at a level above the level of liquid therein.

16. A method as claimed in claim 15, wherein said portion of said liquid withdrawn from said lower region of the chamber is recycled to the chamber at a rate of between 50% and 500% of the through-flow volume of the tank.

* * * * *